United States Patent [19]
Goodman et al.

[11] Patent Number: 5,415,626
[45] Date of Patent: May 16, 1995

[54] TWO PIECE RELEASABLE BANDAGE

[75] Inventors: Greg R. Goodman, Dallas, Tex.; Drew D. Weaver, Sandy, Utah

[73] Assignee: MegaDyne Medical Products, Inc., Draper, Utah

[21] Appl. No.: 83,985

[22] Filed: Jun. 25, 1993

[51] Int. Cl.⁶ .................................................. A61F 3/00
[52] U.S. Cl. ........................................ 602/57; 602/41; 128/887
[58] Field of Search ............... 602/57, 41, 42, 43, 602/52, 53, 54; 128/896, 887, 888

[56] References Cited

U.S. PATENT DOCUMENTS

| | | | |
|---|---|---|---|
| 3,490,448 | 1/1970 | Grubb | 602/53 |
| 4,245,630 | 1/1981 | Lloyd et al. | 602/93 X |
| 4,450,845 | 5/1984 | Engel | 128/846 X |
| 5,086,783 | 2/1992 | Hathman | 128/887 X |

FOREIGN PATENT DOCUMENTS 306464  3/1989  European Pat. Off. .............. 602/91

*Primary Examiner*—Sam Rimell
*Attorney, Agent, or Firm*—John L. Sigalos

[57] ABSTRACT

A two-piece bandage for placing on each side and over a wound, includes two pieces of material having an adhesive on one side to adhere to the skin. A first piece of the bandage has an adhesive layer covering one end of the bottom side of the bandage, and another end of the bottom side that overlies the wound, and does not have adhesive thereon except at the edge. A small peel strip covers the edge having the adhesive thereon. A second piece of the bandage is a strip of material having a bottom side covered with adhesive, and a strip of plastic material on one end of the top, non-adhesive, side.

11 Claims, 4 Drawing Sheets

TWO PIECE RELEASABLE BANDAGE

FIELD OF THE INVENTION

This invention relates to bandages for covering wounds, and more particularly to a two piece bandage that may be opened to allow exposure and examination of a wound, and then closed to protect the wound.

BACKGROUND OF THE INVENTION

Bandages for protecting and covering wounds are available in several configurations. The simplest type bandage commonly used is the single strip of material with an adhesive on one side and a non-adhesive material in the middle portion of the strip. This type of bandage is commonly called an "adhesive bandage". Such bandages may be used only once. If the bandage is removed from attachment to the skin, it usually will not properly adhere again.

A two-piece bandage manufactured by Johnson and Johnson, and referred to as the "Montgomery Strap" utilizes two adhesive strips that are placed on two sides of a wound. Each strip has a plurality of holes in the strip adjacent the ends of the strips placed adjacent the wound. A string or lacing strip is threaded through the holes to hold gauze or other material in place over the wound. Lacing and unlacing to cover or uncover the wound is time consuming, and may be painful to the wounded person since the activity of lacing and unlacing may be accompanied by pressure on the wound.

SUMMARY OF THE INVENTION

The invention is a two-piece bandage that includes two pieces of material having an adhesive on one side to adhere to the skin. A first piece of the bandage has an adhesive layer covering one end of the bottom side of the bandage, and another end of the bottom side that overlies the wound, and does not have adhesive thereon except at the edge. A small peel strip covers the edge having the adhesive thereon.

A second piece of bandage has an adhesive layer covering one end of the bottom side of the bandage, and another end of the bottom side overlies the wound, and does not have adhesive thereon. A strip of plastic material covers one end of the top, non-adhesive, side.

The first piece of the bandage is placed adjacent to a wound with the non-adhesive end overlying the wound. The second piece of the bandage is placed on the opposite side of the wound from the first piece. The edge of the non-adhesive end of the first piece overlaps the second piece of the bandage, and the adhesive at the edge adheres to the strip of plastic on the top of the second piece.

The adhesive on the end of the first piece of the bandage may be repeatedly attached to and peeled from the strip of plastic on the second piece, allowing the wound to be quickly uncovered for treatment and then recovered. In the event that liquids or other material is spilled on the plastic strip on the second piece of the bandage, it may be wiped clean prior to closing the bandage, preventing contamination of the adhesive on the edge of the first part of the bandage.

In a specific embodiment the two piece openable and closable bandage, includes: a first bandage strip having an adhesive backing on a part of one side of a first end, and an adhesive strip along a second end, the adhesive backing on one side of a first end and the adhesive strip along a second end separated by a non-adhesive area for overlying a wound; a second bandage strip having an adhesive backing on one end of one side and a non-adhesive end on said one side, and a non-contaminating strip of plastic on one end of a second side; and a lift tab on said second end of said first bandage strip for lifting said non-adhesive area of said first strip from, and exposing the wound; whereby said first and second adhesive strips are placed on opposite sides of a wound, with the non-adhesive area of one of said bandage strips over the wound, and the adhesive strip along a second end of said first bandage strip adhered to the non-contaminating strip of plastic on one end of a second side of said second bandage strip.

The technical advance represented by the invention, as well as the objects thereof, will become apparent from the following description of a preferred embodiment of the invention when considered in conjunction with the accompanying drawings, and the novel features set forth in the appended claims.

DESCRIPTION OF A PREFERRED EMBODIMENT

Figure 1:
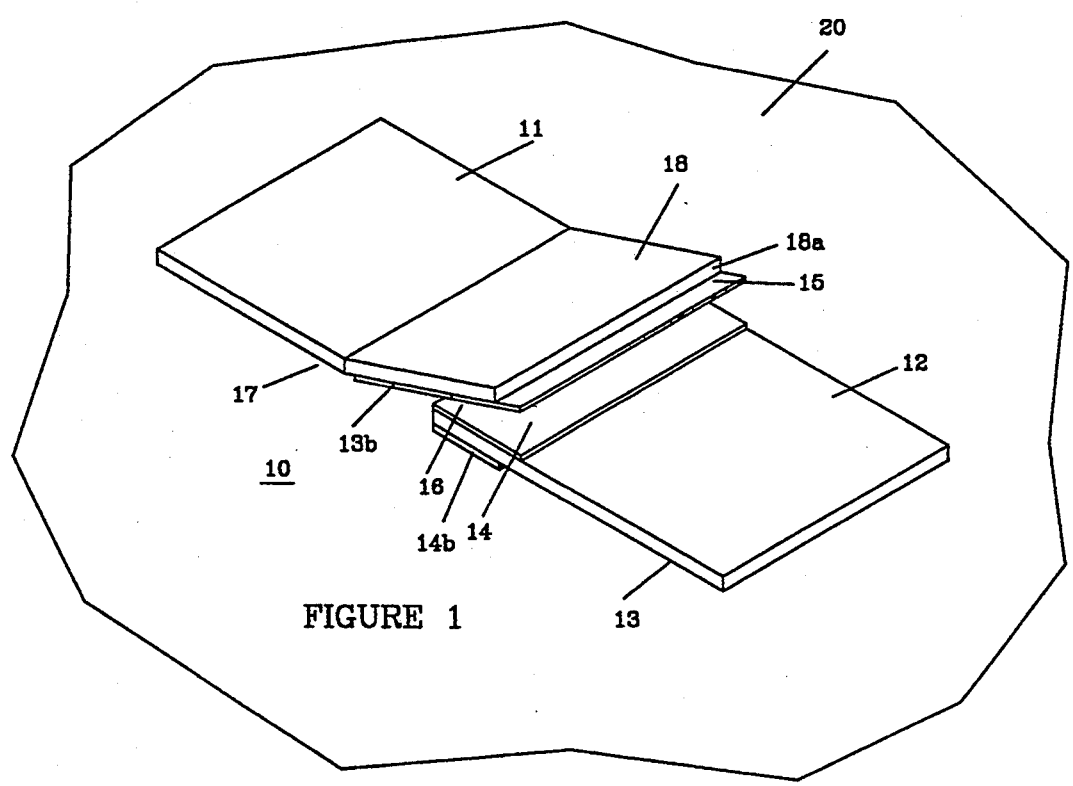
FIG. 1 is an isometric view of the bandage of the invention.

FIG. 1 is an isometric representation of the present invention. Bandage 10 is applied to a body part 20 over a cut or other wound. Bandage 10 has two basic parts 11 and 12. Part 11 has one side coated with an adhesive (17a, FIG. 2) and the adhesive is adhered to body part 20 on one side of the wound. End 18 of part 11 does not have an adhesive on the underside except at the edge with is covered which a pull strip 15. Lift strip 16 is used to lift end 18 away from the wound and the top of part 12.

Part 12 has an adhesive (13a, FIG. 2) on its underside which is adhered to body part 20, on a side of the wound opposite bandage part 11. Part 12 also has a strip of plastic material 14 on the topside of part 12, at one end. The adhesive on the under side of end 18a (underside of 16a, FIG. 2) sticks to plastic strip 14 when the bandage is closed. Lift tab 16 on end 18a utilizes easy lifting of end 18 from part 12.

Bandage parts 18b and 14b are non-adhesive plastic strips that are over the wound and adjacent areas.

Figure 2:
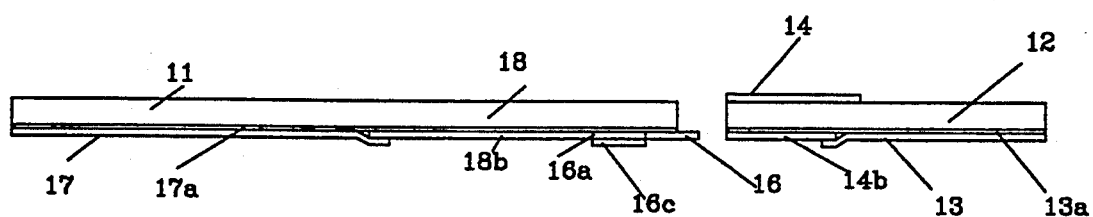
FIG. 2 is a side view of one embodiment of the bandage.

FIG. 2 is a side view of one embodiment of the two piece bandage prior to application over a wound. Part 11 has an adhesive 17a applied to the bottom side of the bandage. A pull strip 17 covers part of adhesive 17a to protect it from contamination prior to use of the bandage. The underside of 18 has a strip 18b which overlays, at least in part, the wound to be covered by the bandage. Strip 16a, when assembled over the wound with bandage part 12, covers and adheres to part 14. Strip 16a has an adhesive on its under side which removably adheres to strip 14 on bandage part 12. Strip 16a has protective cover 16c that is removed prior to use. Strip 16 is used as a lift tab to facilitate lifting bandage end 18 from off the wound area.

The second part 12 of the bandage has an adhesive 13a on the underside covered by pull strip 13. A strip of plastic material 14 is placed along one edge on the top side. Strip 14 is used in conjunction with 16a to provide a resealable fastener.

Figure 2A:
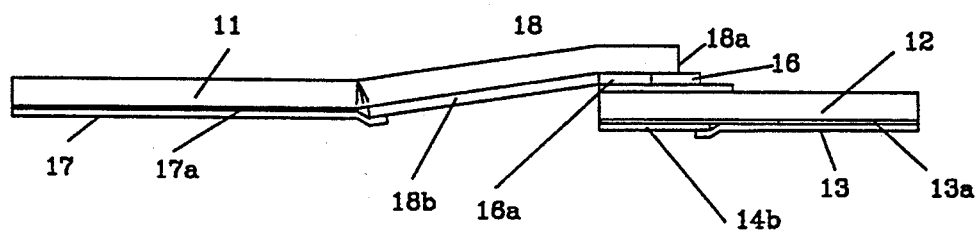
FIG. 2A is a side view of still another embodiment of the bandage.

In the embodiment of FIG. 2A, end 18 of part 11 overlays strip 14 as it does when the bandage is placed over a wound. The advantage of this embodiment is that the bandage is sold as one piece and is ready to apply over the wound after protective pull strips 13 and 17 are removed.

As an example, the main body of the bandage, parts 11 and 12 may be, for example, a medical grade white taffeta coated on one side with a medical grade acrylic pressure-sensitive adhesive. An example of such material is dermaFLEX TAFFETA, designated as #H-520 90 PFW, manufactured by Flexcon Company. An adhesive has been applied to one side and covered with coated paper to protect the adhesive prior to use. Any similar product may be used.

The second part 12 is the same material as part 11 with the exception that a strip of plastic film 14, for example 3M Company product 1516, is applied to the top adjacent to the adhesive end 18a. Adhesive 13a, on the bottom side of part 12, is protected by pull strip 13. Plastic strip 14b may be of the same material as strip 18b.

Parts 14, 14b, 16, and 18b may be, for example, one mil thick polyester film. Part 16a may be, for example, a three mil thick strip of polyethylene film coated both sides with a hypoallergenic pressure sensitive acrylate adhesive.

Figure 3:
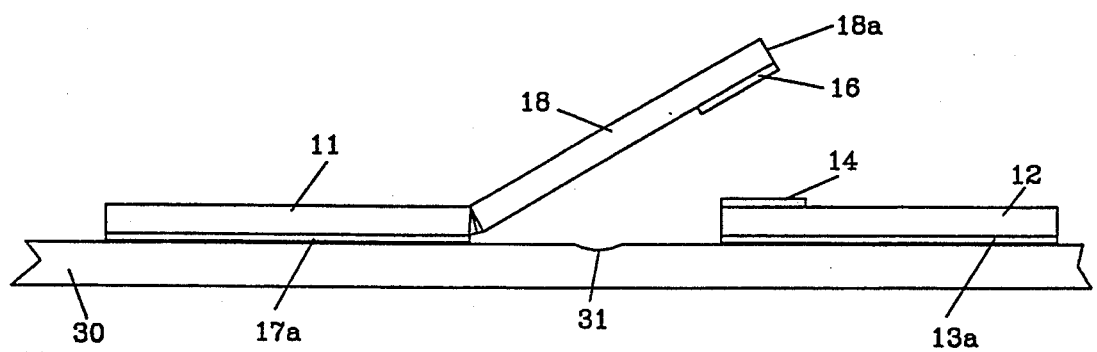
FIG. 3 is a side view of the bandage in an open position after application of the bandage to a wound.

FIG. 3 illustrates the two-part bandage 10 over a wound 31 on a body part 30 with the end 18 of part 11 open. Bandage part 11 is positioned adjacent to wound 31 with part 11 adhered to the surface of body 30 by adhesive 17a. Bandage part 12 is positioned adjacent to wound 31, but on the opposite side from bandage part 11. Adhesive 13a adheres part 12 to body surface 30. The two parts are positioned so that end 18a of bandage part 11 overlaps one end of bandage part 12.

Figure 4:
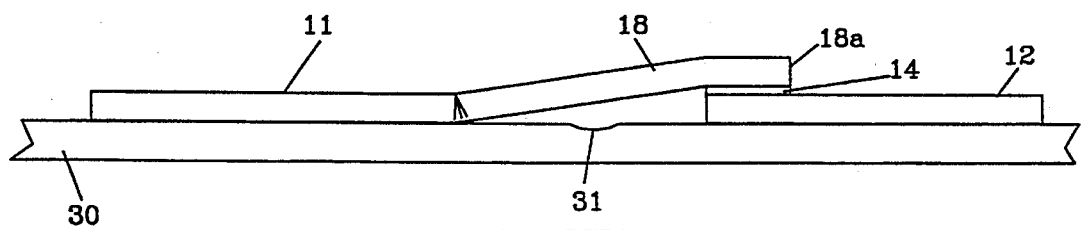
FIG. 4 illustrates the bandage in a closed position over a wound.

FIG. 4 illustrates bandage 10 closed over wound 31. Bandage part 11, end 18, is moved downward over wound 31 until an adhesive (not illustrated) on the bottom of strip 16a adheres to plastic strip 14. When the wound is to be examined or treated, end 18 of bandage part 11 is lifted by lift tab 16 (FIG. 2A). If, during treatment or examination, a liquid or other material should be applied to plastic strip 14, the material is removed by wiping strip 14, and end 18 is resealed against strip 14 by the adhesive on the bottom of strip 16. The adhesive is formulated so that it may be repeatedly resealed against an appropriate surface.

Figure 5:
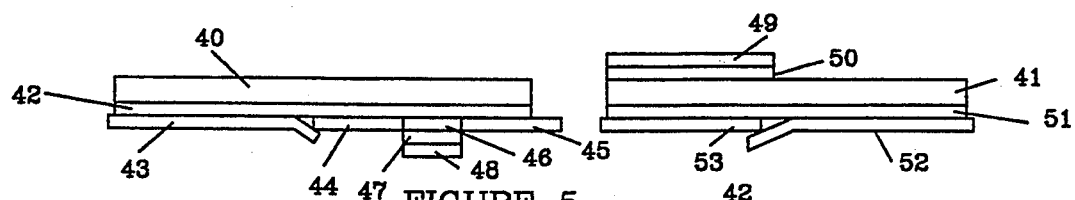
FIG. 5 illustrates another embodiment of the bandage with exaggerated component sizes to illustrate the construction of the bandage.

FIG. 5 illustrates another embodiment of the invention wherein the right side, as viewed in FIG. 5, covers the wound. The dimensions of each component of the bandage have been exaggerated to clearly show the different components. In FIG. 5, the principal part of the left side of the bandage is, for example, a medical grade white acetate 40 with a medical grade hypoallergenic acrylic pressure-sensitive adhesive 42 applied to the underside. A polyethylene coated paper release liner 43 covers a part of adhesive 42. Part 44 is, for example a one mil thick polyester film adhered to adhesive 42. Film 44 may, at least partially contact the wound or a dressing over the wound. A three mil transparent film 47 has an adhesive 46 on its top side to adhere it to adhesive 42. On the bottom side of film 47 is adhesive 48. Film 45 is adhered to adhesive 42 and is used as a pull tab to open the bandage when it is closed over a wound.

The right side of the bandage includes bandage part 41 having an adhesive 51 on the bottom side. Adhesive is partially covered with a paper liner 52 and with a polyester film 53. On the top side and at one end of bandage 41 is an adhesive 50 to which is adhered a polyester film 49.

Figure 6:
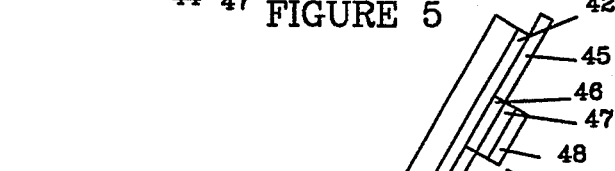
FIG. 6 is the bandage of FIG. 5 being applied over a wound.
Figure 6:
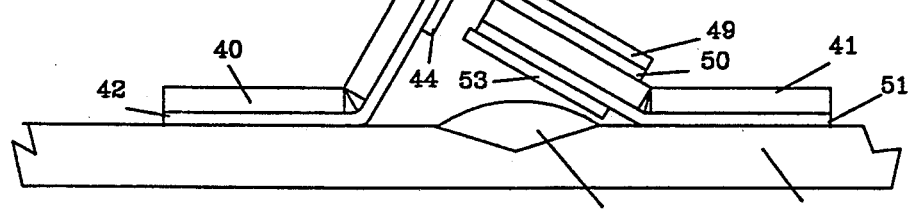

FIG. 6 is the bandage of FIG. 5 being applied over a wound on body part 60. The wound is covered with a dressing 61. The right side 41 of the bandage is placed over the wound dressing 61, and the left side 42 of the bandage is placed over the right side.

Figure 7:
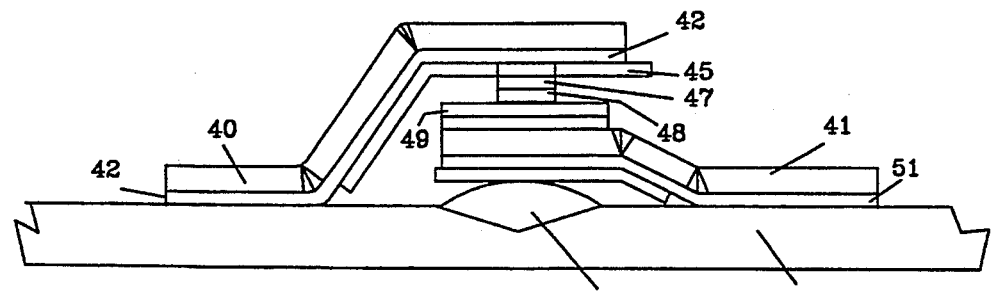
FIG. 7 shows the bandage applied to and over a wound.

In FIG. 7 the bandage is placed over the wound and dressing. Adhesive 48 adheres to film 49 and holds the bandage secure over the wound. Adhesives 42 and 51 hold the bandages secure to the body part 60.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

What is claimed:

1. A two-piece openable and closable bandage, comprising:
   a first bandage strip having an adhesive backing on a first end of one side and an adhesive strip along a second end, the adhesive backing on one side of a first end and the adhesive strip along a second end separated by a non-adhesive area; and
   a second bandage strip having an adhesive backing on one side and a strip of plastic on one end of a second side;
   wherein each said adhesive backing has a pull strip over the adhesive to protect the adhesive prior to use of the bandage and whereby said first and second adhesive strips are placed on opposite sides of a wound, and the non-adhesive area of said first strip overlays the wound.

2. The bandage according to claim 1, wherein said adhesive strip along a second end adheres to said strip of plastic on one end of a second side of said second bandage strip to hold the non-adhesive area on said first bandage strip closed over said wound.

3. The bandage according to claim 1, wherein said strip of plastic on one end of a second side of said second bandage has an adhesive on one side to adhere the plastic strip to said second bandage strip, and a non-contaminating surface on a second side opposite said one side.

4. The bandage according to claim 3, wherein said non-contaminating surface is cleanable to remove any contaminating materials from the surface prior to sealing and resealing the bandage over the wound.

5. The bandage according to claim 1, including a lift tab on said second end of said first bandage strip for lifting said non-adhesive area of said first strip from over and exposing the wound.

6. A two-piece openable and closable bandage, comprising:
- a first bandage strip having an adhesive backing on a first end of one side, and an adhesive strip along a second end, the adhesive backing on one side of a first end and the adhesive strip along a second end separated by a non-adhesive area for overlying a wound; and
- a second bandage strip having an adhesive backing on one side and a non-contaminating strip of plastic on one end of a second side;
- wherein each said adhesive backing has a pull strip over the adhesive to protect the adhesive prior to use of the bandage and whereby said first and second adhesive strips are placed on opposite sides of a wound, with the non-adhesive area of said first bandage strip over the wound, and the adhesive strip along a second end of said first bandage strip adhered to the non-contaminating strip of plastic on one end of a second side of said second bandage strip.

7. The bandage according to claim 6, wherein said strip of plastic on one end of a second side of said second bandage has an adhesive on one side to adhere the plastic strip to said second bandage strip, and a non-contaminating surface on a second side opposite said one side.

8. The bandage according to claim 7, wherein said non-contaminating surface is cleanable to remove any contaminating materials from the surface prior to sealing and resealing the bandage over the wound.

9. The bandage according to claim 6, including a lift tab on said second end of said first bandage strip for lifting said non-adhesive area of said first strip from over and exposing the wound.

10. A two-piece openable and closable bandage, comprising:
- a first bandage strip having an adhesive backing on a first end of one side, and an adhesive strip along a second end, the adhesive backing on one side of a first end and the adhesive strip along a second end separated by a non-adhesive area for overlying a wound;
- a second bandage strip having an adhesive backing on one end of one side and a non-adhesive end on said one side, and a non-contaminating strip of plastic on one end of a second side; and
- a lift tab on said second end of said first bandage strip for lifting said non-adhesive area of said first strip from, and exposing the wound;
- whereby said first and second adhesive strips are placed on opposite sides of a wound, with the non-adhesive area of one of said bandage strips over the wound, and the adhesive strip along a second end of said first bandage strip adhered to the non-contaminating strip of plastic on one end of a second side of said second bandage strip.

11. The bandage according to claim 10, wherein said adhesive strip along a second end of said first bandage is resealable a plurality of times to said non-contaminating strip of plastic on one end of said second bandage strip.

* * * * *